United States Patent [19]

Bauman

[11] Patent Number: 4,679,547
[45] Date of Patent: Jul. 14, 1987

[54] FLUID SUBMERSIBLE LARYNGOSCOPE

[76] Inventor: Jack Bauman, 1677 San Onofre Dr., Pacific Palisades, Calif. 90272

[21] Appl. No.: 830,738

[22] Filed: Feb. 19, 1986

[51] Int. Cl.⁴ ............................................. A61B 1/26
[52] U.S. Cl. ...................................................... 128/10
[58] Field of Search .................... 128/10, 11; 362/118, 362/158, 202

[56] References Cited

U.S. PATENT DOCUMENTS

| | | | |
|---|---|---|---|
| 2,289,226 | 7/1942 | Foregger | 128/11 |
| 2,433,705 | 12/1947 | Palmeter | 128/10 |
| 3,426,749 | 2/1969 | Jephcott | 128/11 |
| 3,579,269 | 5/1971 | Ostensen | 128/11 |
| 3,598,113 | 8/1971 | Moore | 128/11 |
| 3,609,340 | 9/1971 | Habro | 240/41.1 |
| 3,766,909 | 10/1973 | Ozbey | 128/11 |
| 3,771,514 | 11/1973 | Huffman et al. | 128/11 |
| 3,826,248 | 7/1974 | Gobels | 128/11 |
| 4,037,588 | 7/1977 | Heckele | 128/11 |
| 4,112,933 | 9/1978 | Moses | 128/11 |
| 4,114,187 | 9/1978 | Uke | 362/158 |
| 4,114,609 | 9/1977 | Moses | 128/11 |
| 4,273,112 | 6/1981 | Heine et al. | 128/11 |
| 4,295,465 | 10/1981 | Racz et al. | 128/11 |
| 4,306,547 | 12/1981 | Lowell | 128/11 |
| 4,314,551 | 2/1982 | Kadell | 128/11 |
| 4,320,745 | 3/1982 | Bhitiyakul et al. | 128/11 |
| 4,337,761 | 7/1982 | Upster | 128/11 |
| 4,384,570 | 5/1983 | Roberts | 128/4 |
| 4,527,223 | 7/1985 | Maglica | 362/184 |
| 4,565,187 | 1/1986 | Soloway | 128/11 |
| 4,592,343 | 6/1986 | Upster | 128/11 |

Primary Examiner—Kyle L. Howell
Assistant Examiner—Max F. Hindenburg
Attorney, Agent, or Firm—William W. Haefliger

[57] ABSTRACT

A fluid submersible laryngoscope includes a hollow handle to contain a power supply such as dry cell means. A terminal pin is carried by the handle, and structure is provided to place that pin in electrical energy transmitting relation with a light bulb carried by a blade removably attachable to the handle, the blade insertible into a patient's mouth to illuminate the throat area. Sealing structure is provided between the terminal pin and handle to block access of external fluid into the hollow handle, whether or not the blade is attached to the handle, and when the handle is submerged in fluid.

10 Claims, 7 Drawing Figures

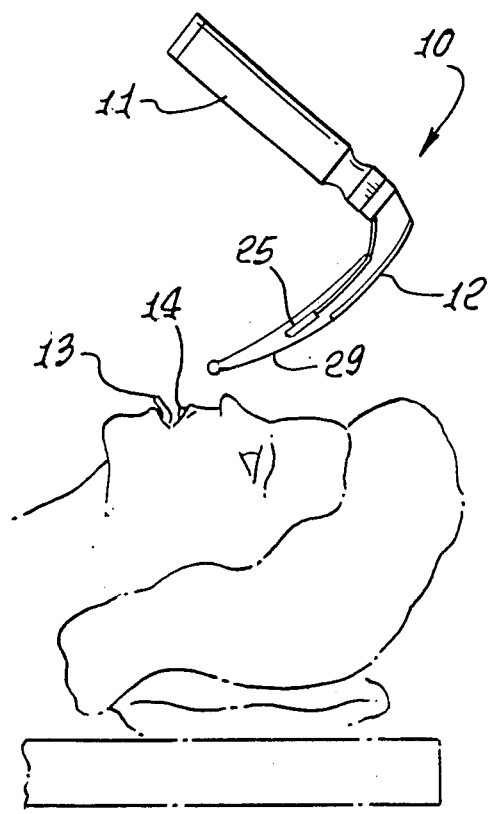
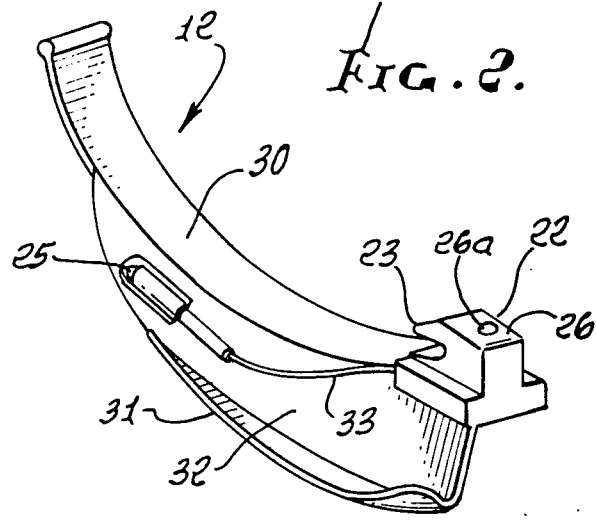
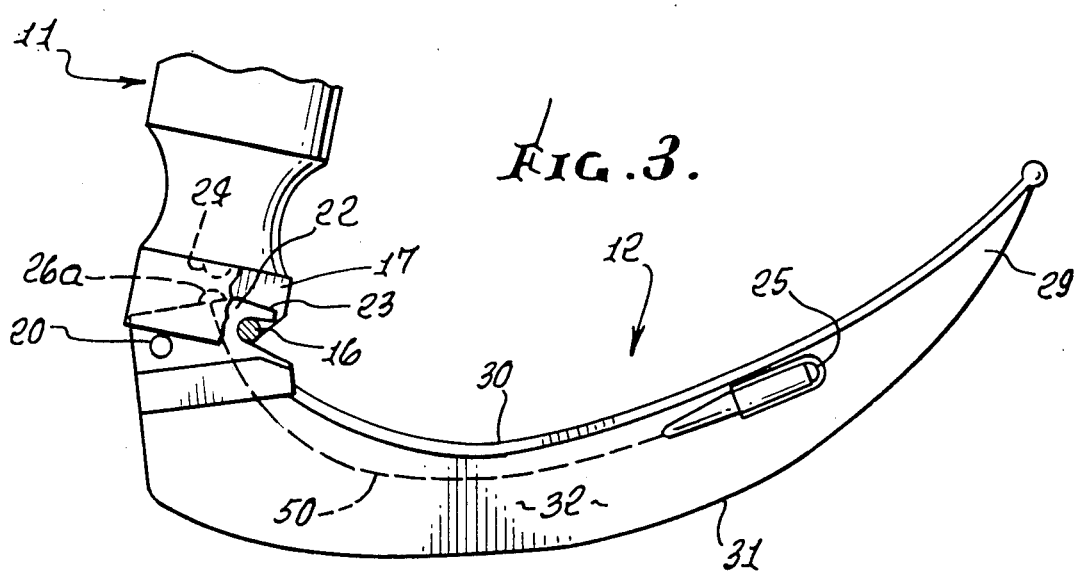

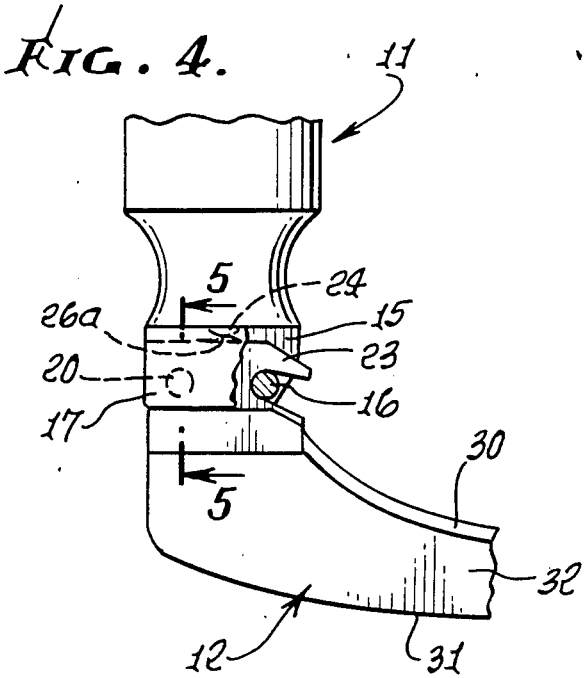
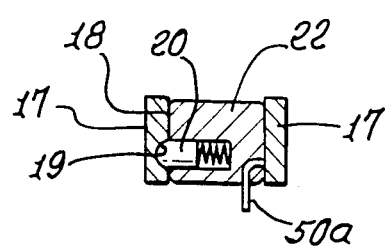
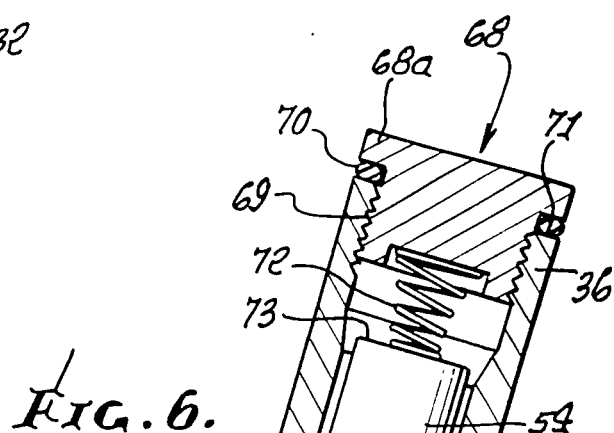
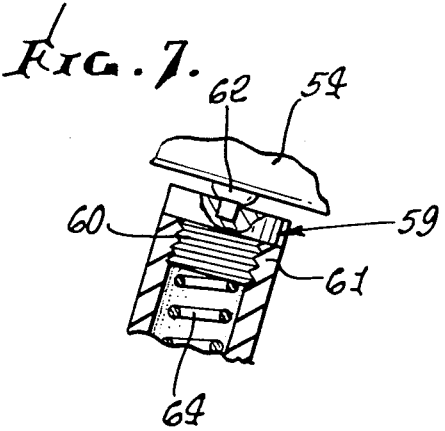

FLUID SUBMERSIBLE LARYNGOSCOPE

BACKGROUND OF THE INVENTION

This invention generally relates to examining devices such as laryngoscopes and particularly to an improved submersible device of this type.

Laryngoscopes generally comprise a blade and a cooperating handle which are connected together in an L-shaped configuration. The hollow handle normally serves as an enclosure for a power supply such as one or more dry cells which are adapted to energize a light bulb. The light from the bulb passes to the distal end of the blade to illuminate the patient's mouth and larynx during the examination thereof by medical personnel. A surface on the blade is used to press against the tongue and mandible of a patient in a supine position in order to prevent the patient's tongue from obstructing the visual examnation of the larynx by medical personnel.

While the instrument is useful for examining the larynx, the primary function of the laryngoscope is to expose the larynx in order to facilitate the insertion of an endotracheal tube. The surface of the laryngoscope blade adjacent the handle is urged against the tongue and mandible to expose the larynx in such procedures and the opposite blade surface is positioned opposing the upper front teeth of the patient.

The handle and blade are desirably re-usable, and must be cleaned thoroughly after use, since fluid from the patient's mouth can contaminate the equipment. However, washing of the handle, presents the problem of fluid gaining access to the power supply, i.e. dry cells, within the handle hollow, as via one or both ends of the handle. This is a particular problem when the light bulb is carried at the end of the handle to which the blade attaches, as cleaning fluid can leak past the bulb into the handle to cause bulb circuit malfunction.

SUMMARY OF THE INVENTION

It is a major object of the invention to provide a solution to the above problem, through provision of a fluid or liquid submersible laryngoscope including a hollow handle to contain power supply means, a blade to be inserted into a patient's mouth, and means to removably attach the blade to an end portion of the handle in a substantially L-shaped configuration, the improvement comprising (a) a terminal pin carried by the handle at said end portion of the handle, (b) means to place the terminal pin in electrical energy transmitting relation with a light bulb carried by the blade, when the blade is attached to the handle, (c) and first fluid sealing means between the terminal pin and handle to block access of external fluid into the hollow handle, whether or not the blade is attached to the handle, and when the handle is submerged in fluid.

As will appear, the fluid sealing means typically comprises a tubular elastomeric body carrying said terminal pin, the pin having a shank in fluid sealing relation with a bore defined by said elastomeric body, said body having an exterior generally annular surface in fluid sealing engagement with a bore defined by the handle. Further, an end closure attached to an end of said body remote from the terminal pin, said closure providing one current passing connection between the power source and said pin; and a compression spring may be provided to extend between the end closure and said pin to provide an electrical current path therebetween, and within said tubular elastomeric body. In this regard, the elastomeric body surface and handle bore preferably have tight, compressed, threaded interconnection to establish a very tight seal therebetween.

Also, an end cap may be removably attached to the end of the handle, remote from the blade, and second fluid sealing means between the cap and handle to block access of external fluid into the hollow handle. In this regard, the handle and end cap are typically metallic, and the second fluid sealing means comprises an elastomeric O-ring. The blade itself is metallic and may carry the light bulb.

These and other features and advantages of the invention will become more apparent from the following detailed description when taken in conjunction with the accompanying drawings:

BRIEF DESCRIPTION OF THE DRAWINGS

FIG. 1 is a side elevational view of a laryngoscope preparatory to being used on a patient which embodies features of the invention;

FIG. 2 is a perspective enlarged view of the blade of the laryngoscope shown in FIG. 1;

FIG. 3 is a side elevational view partially in section, of the laryngoscope with the blade in a ready position;

FIG. 4 is a partial side elevational view, partially in section, of the laryngoscope with the blade in the operative position;

FIG. 5 is a cross sectional view taken along the lines of 5—5 shown in FIG. 4.

FIG. 6 is a cross sectional view of the handle; and

FIG. 7 is an enlarged view of dry cell engagement with an end closure.

In these drawings, all corresponding parts are numbered the same.

DETAILED DESCRIPTION OF THE INVENTION

Reference is made to the drawings which illustrate a laryngoscope embodying features of the present invention. The instrument is intended for use by medical personnel in the examination of a patient's mouth and larynx and particularly to expose the larynx to facilitate the insertion of an endotracheal tube. As shown in FIG. 1, the laryngoscope 10, which comprises a handle 11 and blade 12, is utilized to depress the patient's tongue and mandible 13. Frequently, the patient's front teeth 14 are used as a fulcrum for the blade 12 in order to more completely expose the patient's larynx during the examination of the larynx and the insertion of an endotracheal tube.

One form of means used to couple the blade 11 to the handle 12 is illustrated in FIGS. 2-6. As shown therein, the upper end of the handle 11 has an open channel 15, which is provided with a pivot rod 16 extending between flanges 17. The inner side of one flange has a groove or dimple 19 adapted to seat a spring urged detent 20 projecting at one side surface 18 of of boot-shaped appendage 22 or the blade.

The boot shaped appendage 22 interfits into the open channel 15 and is mounted therein in a pivotal fashion. The front end 23 of the boot shaped appendage 22 is hooked under the pivot rod 16 during the pivotal mounting thereof, in a conventional fashion. To mount the blade onto the handle 11, the appendage 22 of the blade 12 is inserted into the open top channel 15 with a pivotal motion so that the front end 23 rotates under the pivot rod 16 i.e. from FIG. 3 to FIG. 4 condition. The detent 20 moves into engagement with the groove 19 provided in the surface 18, to thereby snap retainer appendage 22 in firm interfit with the pivot rod 16, as the blade moves from ready position, as shown in FIG. 3, to fixed position seen in FIG. 4.

Preferably, a light switch or contact 24 is provided at the bottom of the channel 15 in a position so that it is activated only when the blade 12 is rotated and locked into an operating position. A light source 25 such as an incandescent bulb is provided on the blade and is energized when the light switch 24 is activated. As shown in FIG. 3, when the blade 12 is initially mounted on the handle 11, the blade 11 is in a ready position on the handle 12 but a contact 26a on the bottom surface 26 of the appendage 22 does not activate, i.e. engage the light switch. Further rotation of the blade 12 causes the detent 20 to engage the groove 19, and to thereby lock the blade 12 in an operating position and simultaneously therewith to cause contact 26a to engage, i.e. activate the light switch 24, which in turn energizes the light source 25. Wiring 50 extends from contact 26a to the bulb and may include a ground wire 50a returning to engage the metal of channel flange 17 (see FIG. 5). Metal channel 33 on the blade protectively confines wiring 50 and is carried by web 32.

As best shown in FIGS. 2-4, light is directed from the light source 25 to ensure the proper illumination of a patient's mouth and larynx when the laryngoscope is being used. The light, at the proximal end of a light conductor, is located near the end 29 of the blade 12 so that, when the blade 12 is rotated into its final operating position, the contact 26a is immediately adjacent to and engages the terminal 24 so that there is a reliable and efficient electrical coupling therebetween, to provide electrical energization of the light bulb 25 or light conductor.

The lower portion 30 of the blade 12 which comes in contact with the tongue and mandible 13 of the patient should be rigid, whereas the upper section 31 comes in contact with the patient's teeth 14. Surface 31 which is in contact with the patient's teeth 14 is supported to the rigid portion 30 of the blade 12 by means of the wall or web 32.

The handle 11, which is typically metallic, has an internal cavity 11a which is adapted to hold one or more battery units 54 (see FIG. 6) which supply elelctrical energy to light source 25.

The handle comprises a tubular body 34 having a reduced diameter end 35, and opposite end 36. The contact 24 is advantageously formed at the head of a terminal pin 37 located at handle end 35. The pin is placed in electrical energy transmitting relation with the light source, by means such as that referred to above.

Also provided is first fluid sealing means, located between the terminal pin and handle to block access to external fluid into the hollow handle, whether or not the blade is attached to the handle, and when the handle is submerged in fluid. As shown, the first fluid sealing means comprises a tubular elastomeric body 55 carrying the terminal pin, the conductive pin having a shank 37a in fluid sealing relation with a bore 56 defined by the elastomeric body 55, the latter having an exterior generally annular surface 57 in fluid sealing engagement with a bore 58 defined by the handle. Surfaces 57 and 58 may advantageously be threaded, and be in tight compressive engagement to define a good fluid seal.

Also shown is an end closure 59 attached as by threading 60 to an end 61 to said body remote from the terminal 24, said closure providing a current passing connection between the power source and said pin. Note that dry cell terminal 62 engages conductive metallic closure 59, which is carried on the insulative body 57.

A metallic and conductive compression spring 64 extends between said end closure 59 and said pin 37, to provide an electrical current path therebetween, and within said protective and insulative tubular elastomeric body 55.

A thin, synthetic resin sleeve 65 protectively extends about the shank 37a and is compressed between that shank and the bore 55a of the elastomeric body. The head 55b of body 55 is enlarged to provide firm mount for the pin 37 and the reduced diameter extent 55c of the body, which mounts closure 59, so that elastomeric shank 55c can withstand loading imposed by the batteries 54.

An end cap 68 is removably attached to the end 36 of the handle, remote from the blade, and second fluid sealing means is provided between the cap and handle to block access of external fluid into the hollow handle, via end 36. In this regard, the cap may have threaded attachement at 69 to the handle, the cap and handle and typically metallic. Said second fluid sealing means may comprise an elastomeric O-ring 70 compressed between cap flange 68a and handle end 71 to establish a ground. Element 70 may be a rubber washer.

A coil spring 72 is located between the cap 68 and the end 73 of one battery 54.

After use, the blade is decoupled from the handle by simply rotating the blade 12 toward the handle 11 and then pushing upwardly on the blade 12 to disengage or unhook the front end 12 of appendage 22 from the pivot rod 16. The blade being formed from metal, can be sterilized and reused, as is the handle Although the specific embodiment of the invention is described herein in connection with laryngoscopes, it is clear the the improved means to connect a blade and a handle into an L-shaped configuration can be employed in other examining devices.

It will be noted that the body 55, being of compressible material, provides "after-travel" or spring-like action to the terminal pin for improved blade terminal contact.

Modifications and improvements can be made to the present invention without departing from the inventive concepts thereof. One modification is to make the blade of molded plastic (for throw away).

I claim:

1. In a fluid submersible laryngoscope including a hollow handle to contain power supply means, a blade to be inserted into a patient's mouth, and means to removably attach the blade to an end portion of the handle in a substantially L shaped configuration, the improvement comprising:
   (a) a terminal pin carried by the handle at said end portion of the handle,
   (b) means to place the terminal pin in electrical energy transmitting relation with light bulb carried by the blade, when the blade is attached to the handle,
   (c) and first fluid sealing means between the terminal pin and handle to block access of external fluid into the hollow handle, whether or not the blade is attached to the handle, and when the handle is submerged in fluid, (d) said fluid sealing means comprising a tubular elastomeric body carrying said terminal pin, the pin having an enclosed shank in fluid sealing and retained relation with a bore defined by said elastomeric body whereby center extent of the elastomeric body is resiliently yieldable axially of the handle to allow the pin and said center extent of the body to deflect axially when the blade is fully attached to the handle and said electrical energy transmitting relation is established to energize the bulb, the pin having ahead on the shank projecting endwise outwardly of said elastomeric body, said body having an exterior generally annular surface in fluid sealing engagement with a bore defined by the handle.

2. The improvement of claim 1 wherein the tubular body is spaced radially inwardly from the handle along body length between said enlarged shank and a power supply to a accomodate said deflection.

3. The improvement of claim 1 including an end closure attached to an end of said body remote from the terminal pin, said closure providing one current passing connection between a power source and said pin.

4. The improvement of claim 3 including a compression spring extending between said end closure and said pin to provide an electrical current path therebetween, and within said tubular elastomeric body, the body being compressible to resiliently transmit force for improved contact of the pin with a surface on the blade.

5. The improvement of claim 1 wherein said body surface and handle bore have threaded interconnection.

6. The improvement of claim 5 including a synthetic resinous sleeve extending about said pin shank and compressed between said shank and the bore of said elastomeric body.

7. The improvement of claim 1 including an end cap removably attached to the end of the handle, remote from the blade, and second fluid sealing means between the cap and handle to block access of external fluid into the hollow handle.

8. The improvement of claim 7 wherein the handle and cap are metallic, and said second fluid sealing means comprises an elastomeric O-ring.

9. The improvement of claim 1 wherein the blade consists the synthetic resinous material, and has a bite flange thereon.

10. The improvement of claim 1 wherein the bulb is carried by the blade near the end thereof remote from the handle.

* * * * *